United States Patent [19]

Munk et al.

[11] Patent Number: 5,277,707

[45] Date of Patent: Jan. 11, 1994

[54] AIR STREAM SOLVENT VAPOR REMOVER

[75] Inventors: Michael Munk, Stamford, Conn.; Carlo Garanzini, Monza, Italy; Louis H. Reens, 281 Cheese Spring Rd., Wilton, Conn. 06897

[73] Assignees: Cool Fog Systems, Inc., Norwalk; Louis H. Reens, Wilton, both of Conn.

[21] Appl. No.: 916,961

[22] Filed: Jul. 16, 1992

[51] Int. Cl.$^5$ .................. B01D 53/14; B01D 47/06
[52] U.S. Cl. ................................. 95/8; 95/228; 95/239; 55/222; 55/223; 55/226; 55/269; 55/277
[58] Field of Search .............. 55/15, 80, 84, 85, 87, 55/89, 222, 223, 226, 267, 269, 274, 277

[56] References Cited

U.S. PATENT DOCUMENTS

| | | | |
|---|---|---|---|
| 1,889,161 | 11/1932 | Thomas . | |
| 2,207,774 | 7/1940 | Barthelemy | 55/87 X |
| 2,720,939 | 10/1955 | Stokes | 55/15 |
| 3,473,298 | 10/1969 | Berman | 55/222 |
| 3,494,099 | 2/1970 | Eng et al. | 55/8 |
| 3,593,496 | 7/1971 | Merrill | 55/77 |
| 3,704,570 | 12/1972 | Gardenier | 55/84 |
| 3,726,062 | 4/1973 | Hungate et al. | 55/89 |
| 3,755,990 | 9/1973 | Hardison | 55/93 |
| 3,762,394 | 10/1973 | Newcomer | 55/222 X |
| 3,831,294 | 8/1974 | Freze | 34/131 |
| 3,851,822 | 12/1974 | Pocrnja et al. | 55/269 X |
| 3,854,909 | 12/1974 | Hoisington et al. | 55/269 X |
| 3,889,390 | 6/1975 | Klare | 68/18 X |
| 3,894,851 | 7/1975 | Gorman | 55/94 |
| 3,925,040 | 12/1975 | Fattinger | 55/84 X |
| 4,042,016 | 8/1977 | Boochever et al. | 165/20 |
| 4,078,390 | 3/1978 | Duvall | 55/84 X |
| 4,086,705 | 5/1978 | Wehr | 68/18 X |
| 4,118,945 | 10/1978 | Boochever et al. | 165/20 X |
| 4,364,750 | 12/1982 | Koncz | 55/89 |
| 4,378,976 | 4/1983 | Rush | 55/277 X |
| 4,544,380 | 10/1985 | Itou et al. | 55/80 |
| 4,564,375 | 1/1986 | Munk et al. | 55/277 X |
| 4,682,990 | 7/1987 | Kagström et al. | 55/80 |
| 4,704,972 | 11/1987 | Marchand | 55/80 X |
| 4,788,776 | 12/1988 | Führing et al. | 34/76 |
| 4,802,573 | 2/1989 | Hölter et al. | 55/89 X |
| 4,964,885 | 10/1990 | Wieser-Linhart | 55/85 X |

OTHER PUBLICATIONS

Part III: Air Washer, 1988 ASHRAE Handbook, pp. 4.6–4.8.
Perry's Chemical Engineers' Handbook, Sixth Edition, pp. 20–92 to 20–97, "Solids Drying and Gas–Solid Systems".

Primary Examiner—Robert Spitzer
Attorney, Agent, or Firm—St. Onge Steward Johnston & Reens

[57] ABSTRACT

A method and system are described to remove solvent vapors emanating from a source in a work place. The air stream is passed through a fogging chamber in which a plurality of ultrasonic foggers are used to create a supersaturated condition in the form of vapor and droplets of a scrubbing liquid such as water. The supersaturated condition is accompanied with a large amount of turbulence and mixing flows throughout the chamber to reduce the ability of solvent vapors from bypassing contact with the scrubbing liquid. The scrubbing liquid droplets and vapor are then condensed out in a cooling condenser and collected to leave a scrubbed air stream from which a substantial amount of the solvent vapors is removed. The scrubbed cooled air stream may then be recirculated for reuse in the work place. Several embodiments are shown and described including a scrubbing system in which several fogging chambers and condensers are used in tandem for an enhanced removal of solvent vapor from the air stream.

16 Claims, 3 Drawing Sheets

AIR STREAM SOLVENT VAPOR REMOVER

FIELD OF THE INVENTION

This invention generally relates to a system and method for removing solvents from an air stream. More specifically, this invention relates to a system and method for the stripping of solvents which are miscible with or soluble in or have an affinity for water.

BACKGROUND OF THE INVENTION

Humidification of air by use of ultrasonic devices operating within an air handler are well known in the art. See, for example, U.S. Pat. Nos. B1 4,042,016, 4,118,945 and 4,564,375. Typically, these types of systems generate a fog using an ultrasonic device for breaking up a stream of air and water into fine droplets. These droplets preferably evaporate before the air carrying them along reaches filters or other downstream devices, such as cooling coils and the like. The distribution of the fog is normally selected to minimize the amount of air that can bypass mixing with the fog. In some air handlers, the water droplets still reach downstream devices, thereby wetting these with some further humidification arising from the evaporation from the wetted devices. In such case, it is still necessary to provide drainage for water dripping down from the wetted devices. Generally, however, wetting is preferably avoided for bacterial growth prevention and unnecessary loss of water.

In the ultrasonic humidification of the air in or before an air handler, the humidification of the air inside the air handler often achieves levels substantially higher than those within the building areas that are intended to be humidified, so that the humidification level inside the building achieves a desired level. Although saturation levels can occur inside the air handler, saturation preferably is avoided, primarily to prevent condensation on cool metal surfaces and prevent the creation of stagnant pools of water.

U.S. Pat. No. 2,720,939 describes a process of recovering aerosol solids by introducing a liquid such as water as a stable fog or mist so as to cause an agglomeration of the solid particles with water. Agglomeration is enhanced by use of various techniques such as sonic or electrostatic forces. The moisture-laden particles are then condensed out of the air stream by cooling the stream.

U.S. Pat. No. 3,473,298 describes an apparatus for removing air polluting contaminants and condensable vapors from exhaust gas. This involves a spray chamber for generating water in a finely-divided form, a demister for separating water droplets and a condensing tube structure to condense water vapor.

U.S. Pat. No. 3,494,099 describes an apparatus for removing contaminants from a polluted gas stream using an ultrasonic generator which forms a fog in a first zone. An electric field and sound waves are used to cause a three-dimensional oscillatory motion of the vibrating fog droplets. These droplets then are given increased contact time and area to remove contaminants from the polluted gas stream. In a second zone, fm modulated ultrasonic waves are generated to cause an agglomeration of fog droplets and thus removal of solid particles.

U.S. Pat. No. 3,593,496 describes a system for purifying air of organic pollutants by first humidifying the air and mixing this with an aerosol containing pollutants in a mixing chamber. The mixture is subjected to aerosol removal to produce purified air. Other wet scrubber-type contaminants removers are described in U.S. Pat. Nos. 3,704,570 and 3,755,990.

Many of these prior art wet scrubbers require enormous quantities of water to achieve a level of effectiveness. Typically, air washers require spray densities of 1 to 5 gallons per minute per square foot of crossectional area per bank, see the 1988 ASHRAE Equipment handbook on air washers. This, in turn, imposes a greater burden on the disposal or processing of the waste water produced by these wet scrubbers.

Removal from air streams of contaminants such as volatile organic compounds (VOC) is typically accomplished with activated carbon bed filtration systems. These are expensive and complex to use because the activated carbon bed immediately begins to lose effectiveness and needs to be replaced on a regular basis. In a well-maintained, actively-used carbon system, the carbon bed may need to be replaced on a weekly basis. The used carbon bed can be reactivated; however, after repeated activation cycles, the carbon tends to crack and degenerate leading to a loss of a useful, expensive carbon bed and a slip of unabsorbed VOC's.

SUMMARY OF THE INVENTION

In a contaminant removal system, and method in accordance with one aspect of the invention, a gas stream carrying volatized contaminants is passed through a fog chamber. The fog chamber includes a sufficient number of fog generators which in the aggregate produce a well mixed scrubbing vapor that is generally uniformly distributed across the fog chamber so as to minimize the amount of contaminant-laden air that can bypass contact and mixing with to the scrubbing vapor. The fog is introduced preferably into the saturation chamber in such quantity as to produce a supersaturated amount of scrubbing vapor in and across the chamber. Such supersaturation occurs when visible fog exists throughout the chamber. As a result, by the time the contaminant-laden air leaves the chamber, much of the contaminants in the air stream have established contact by absorption, solution or mixture with scrubbing liquid droplets and vapor.

The fog conditioned air stream is then passed through a condenser of a type capable of removing a large and significant amount of the moisture from the air stream by cooling the condenser to a sufficiently low temperature so that air stream vapor condenses. The condensation wets condenser surfaces and moisture droplets tend to adhere to and be captured by the wetted surfaces. The moisture with the contaminants after condensation is collected through a drain stream for disposal or reuse of captured chemicals as well as scrubbing liquid.

The gas stream, if required is heated to increase its ability to absorb scrubbing liquid which, when it is condensed out, is sufficient to maintain a wetted film on condenser surfaces to enhance the capture and subsequent removal of vapor contaminants.

The effectiveness of the contaminants removal with a system and technique of this invention can be sufficient to reuse the air by its recirculation.

With a system and technique in accordance with the invention, local air sources of contaminants are particularly conveniently treated. For example, in a manufacturing plant where a number of different baths containing solvents such as volatile organic compounds (VOC)

are used, care is taken to collect all of the VOCs evaporating from the bath. This typically involves the use of a hood and exhaust ducting and fans which generate sufficient negative pressure to draw ambient air across the bath and entrain the VOCs into the ducting.

With a system and technique in accordance with the invention, substantially most of the VOCs can be removed from the air stream which then can be recirculated by the air handler for the plant at significant heating and cooling seasonal energy cost savings.

A particular advantage of a system and technique in accordance with the invention is that different point of use solvent vapors removal systems can be used for different sources. In this manner, the removed, or stripped solvent can be reclaimed and reused without having to separate it from other different solvents.

As described herein for one air contaminant-removal system and technique in accordance with the invention, a saturated liquid vapor condition in an air stream is generated in a fog chamber with fog generators capable of producing both fog and strong air circulation patterns tending to enhance the mixture of liquid vapor and air and reduce a bypass of the air stream to insignificant levels. This is achieved by using fog generators capable of inducing strong secondary air entrainment resulting in a substantially enhanced mixing action within the chamber and with substantially lower quantities and rates of liquid needed for an effective scrubbing action.

It is, therefore, an object of the invention to provide a system and technique for the removal of liquid-miscible, absorbent or soluble vapors from gas streams. It is a further object of the invention to achieve such removal in a sufficient manner so as to enable a reuse of the air stream by its recirculation. It is a further object of the invention to provide a wet scrubber technique and system which require a substantially lower amount of liquid or water used to scrub an air stream.

These and other objects and advantages of the invention can be understood from the following description of a system and technique in accordance with the invention and illustrated in the drawings.

DETAILED DESCRIPTION OF DRAWINGS

Figure 1:
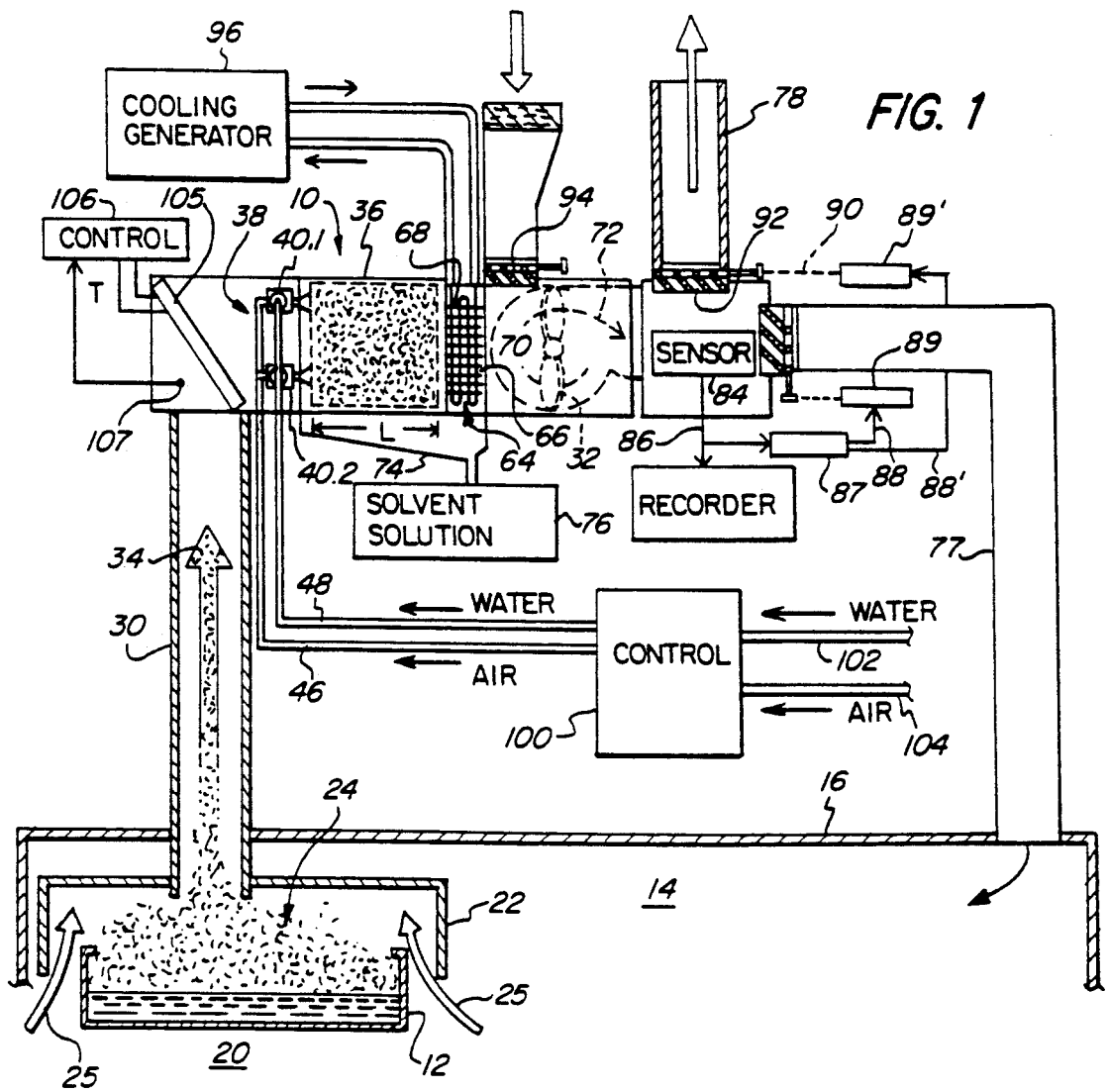
FIG. 1 is a schematic representation and a crossectional view of one system for removing solvent vapors from an air stream in accordance with the invention.

With reference to FIG. 1, a vapor stripper 10 in accordance with the invention is illustrated to remove solvent VOCs from a hooded and vented process bath 12. The bath 12 is located inside a space 14 of a suitable room or ambient area such as a plant 16, the ambient air of which is controlled by a conventional HVAC air handler not shown in the drawing.

As is typical in manufacturing plants, there exists a need to use chemicals for a broad range of purposes. These chemicals can be needed or used in many different forms and work places, such as in a spraying booth, in baths, in processing machines and the like and may be benign or hazardous. When hazardous chemicals must be used, special care has to be taken to reduce emissions lest personnel breathe or are otherwise exposed to undesirably high levels. Typically, a station 20 or a local source where such chemical vapors are generated involves a hood 22 or other suitable enclosure whereby vapors such as 24 from the bath 12 can be collected and safely transported by ducts to a disposal area.

Although it would be convenient to dispose of chemical vapors to the air outside of the plant 16, governmental regulations frequently prohibit such emission. In a system 10 in accordance with the invention, many types of vapors 24 from a local source 20 can be collected. These vapors can then be safely stripped from the air in a manner whereby external emissions are prevented and essentially clean air returned to the space 14. Because of the local collection and treatment by system 10 and capture of these chemicals into relatively small quantities of water as compared with conventional wet scrubbers, the stripped vapors can be economically reclaimed and reused.

In the illustrative embodiment of FIG. 1, a negative pressure is created inside the ducting 30 connected to collection hood 22 by a fan 32. The negative pressure assures that noxious vapors are prevented from reaching work places. The vapors 24 are entrained by the inflow of ambient air 25, typically at room temperature from space 14, to flow as a stream of gas 34 to and through a fog chamber 36.

Inside the fog chamber 36, at its upstream side 38, a suitable number of foggers 40.1, 40.2 are employed. These are oriented and selected to project a substantial fog with fine droplets of liquid, usually water, sufficient to create a thoroughly supersaturated condition within and throughout chamber 36 and thus throughout the crossectional area of the gas stream.

The fog chamber 36 has sufficient length L along the direction of travel of the gas stream 34 to enable both an evaporation of water, or such other scrubbing liquid as may be injected by the foggers 40.1, 40.2 as well as produce an abundance of small droplets. The amount of water vapor and droplets is sufficient to create a condition where the water vapor and droplets can attach to vapor molecules from bath 20 and entrained by the inflow of air 25. This increases the size of the otherwise small untreatable vapor. The condition in chamber 36 is thus at least near saturation and preferably supersaturated with both water vapor, and excess water droplets being actively mixed throughout the volume of chamber 36.

Figure 3:
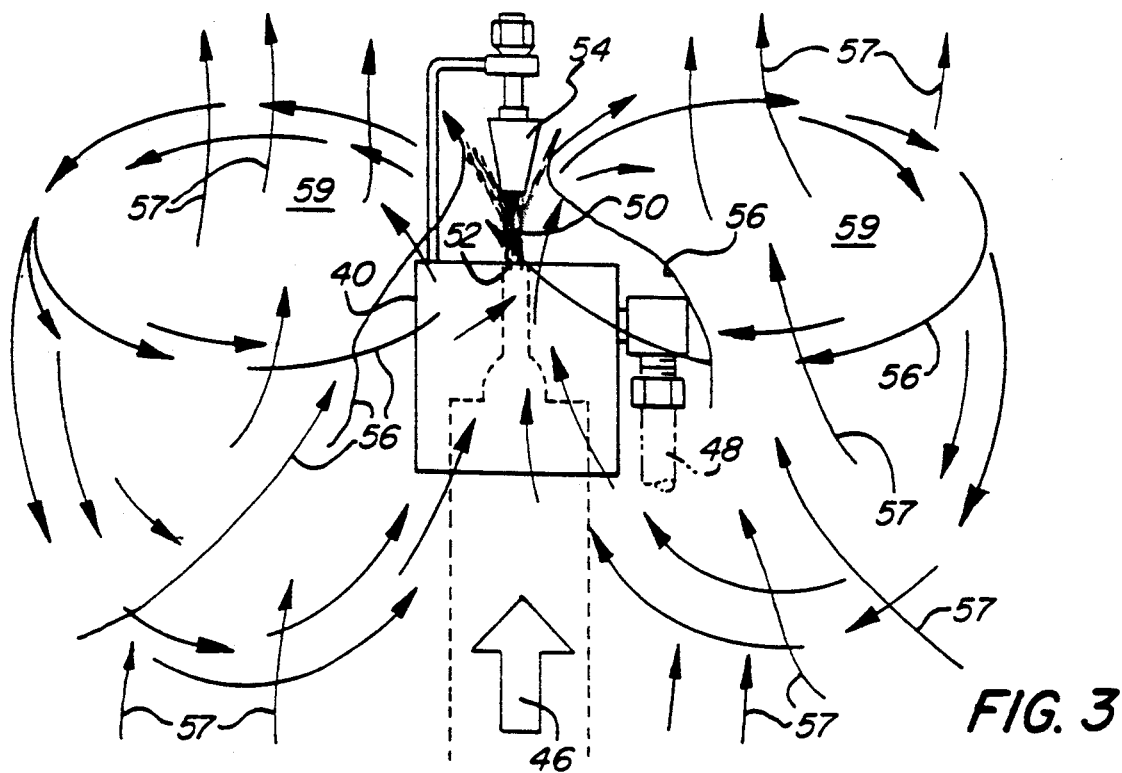
FIG. 3 is a side view of an ultrasonic fogger and air flow in a mode of operation selected to enhance air entrainment and mixture with vapor and droplets introduced by the fogger.
Figure 2:
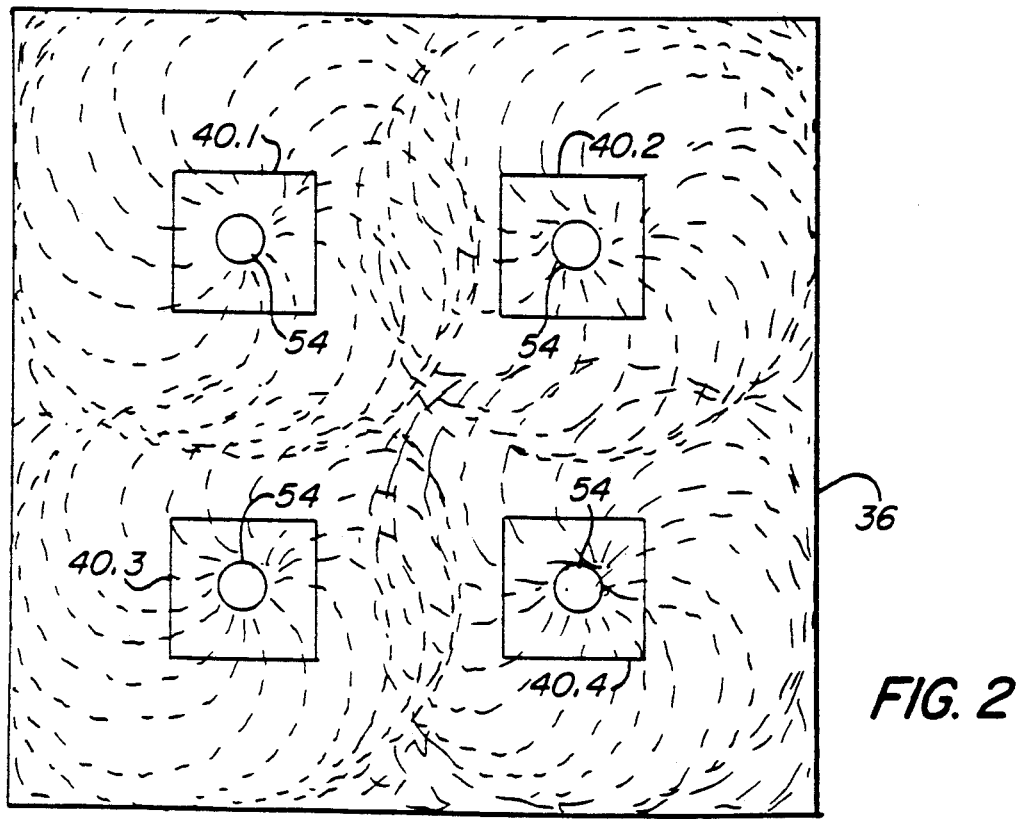
FIG. 2 is a crossectional view of a saturation chamber taken in a direction that is upstream to the flow of the air stream.

Although various types of fogging techniques foggers can be used to saturate chamber 36, a particularly effective fogger 40 is illustrated in FIG. 3 and is more particularly described in a co-pending patent application entitled FOGGER FOR HUMIDIFICATION OF AIR filed by M. Munk on Apr. 30, 1991 and bearing U.S. Ser. No. 07/693,626 and assigned to Cool Fog Systems, Inc. The contents of this patent application and any patent issuing therefrom is incorporated herein by reference.

As illustrated in FIG. 3, the fogger 40 uses a pressurized source of air in line 46 and water in line 48 to produce an ultrasonic stream 50 emanating from an exit port 52. The stream 50 is impacted on a target 54 which is further shaped to promote a heavy flow of secondary air, as suggested by arrows 56 in addition to the primary air flow indicated by arrows 57 to produce a large mixing zone 59. The visible fog pattern produced by fogger 40 can be regulated or tuned by adjusting the position of target 54 with respect to the discharge port 52 to optimize secondary air entrainment and thus increase the amount of mixing in the fog chamber.

The fog pattern preferably is adjusted so as to assure that the entire crossection of the gas stream 34 is exposed to the mixture of water vapor and droplets This involves an adjustment of target 54, or resonator as it is also called, until the fog pattern expands predominantly radially away in all directions from the ultrasonic stream 50 generally transverse to the direction of the main flow of the air stream 34. Such pattern as shown in FIG. 3 also includes a large amount of recirculation of air by way of secondary air entrainment and enhances the exposure of the gas stream 34 inside chamber 36 to a mixture of air and water.

It is desirable that virtually all of the gas stream 34 inside chamber 36 is exposed to water vapor and droplets with a minimum or virtually no bypass factor. By bypass factor, it is meant that percentage of the crossectional area of the gas stream 34 that would not be exposed to a mixture of vapor and droplets within chamber 36. One technique for achieving a low bypass factor involves the selection of a preferred operating condition for foggers such as 40. In a typical humidification application, foggers 40 are operated within a range of air pressure needed to establish at most a dry vapor condition without droplets. This typically involves air pressures in the range from about 30 to about 60 psi. At these pressures, the emanating ultrasonic stream 50 produces a controlled secondary air flow and thus enhanced mixing action.

Figure 4:
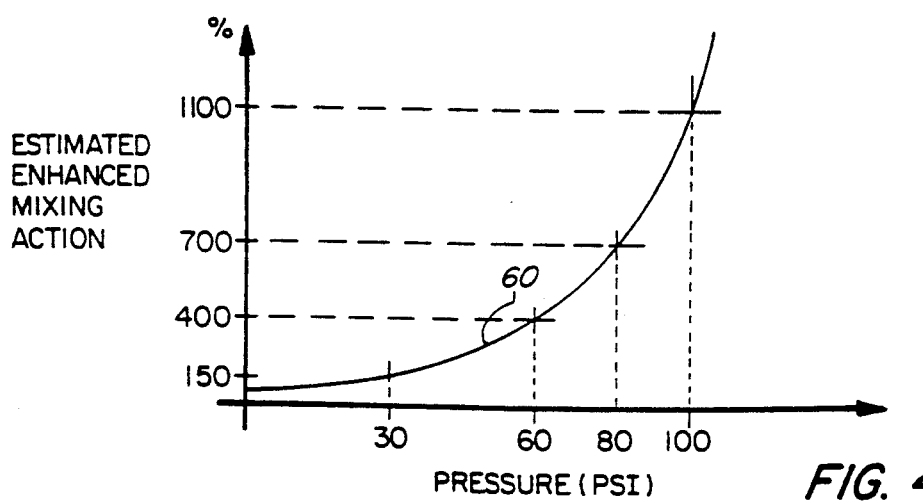
FIG. 4 is an operating curve for a fogger illustrating the effect of air pressure on secondary air entrainment.

By operating foggers such as 40 at a significantly higher air pressure, the amount and strength of secondary air flow is enhanced and consequently a substantially greater amount of air, water vapor, and droplet mixing occurs throughout the saturation chamber 36. The increase in the mixing effect as a function of pressure of the air 46 can be appreciated with the curve 60 in FIG. 4. The curve 60 is an estimate of the mixing enhancement introduced when the air pressure for a fogger is increased. The estimate is based upon the increase of the entrained secondary air mass flow relative to the primary air mass flow. By operating a fogger 40 at an air pressure between above 60 psi and as high as 100 psi, a substantial enhancement of the fog pattern and the mixing in chamber 36 is obtained. The enhanced mixing in turn significantly improves the probability that solvent vapor molecules which are miscible with soluble in or have an affinity for water become attached to a water molecule or droplet within chamber 36, thus creating a larger treatable or extractable particle.

Another technique for assuring a thorough fogging and mixing action in chamber 36 involves the use of highly pressurized steam. Such steam can be introduced for example through foggers such as 40 by applying steam only at pressures that can be from about four to about eight or greater bars (atmospheric pressures). Steam can also be introduced by applying it with jets generated from small orifices drilled along steam distributor pipes. The orifices transform the energy of the highly pressurized steam into high velocity jet capable of inducing secondary air entrainment to duplicate the mixing affect of the foggers 40 in chamber 36.

As the supersaturated water vapor and droplet-laden gas stream 34 leaves chamber 30, the stream enters a condenser 64. This can be of the multiple coil 66 and fin 68 type wherein chilled water or other coolant enters the downstream side 70 of the condenser 64 and exits toward the opposite upstream side. The temperature of the coolant and the size of the condenser are selected so that most or virtually all of the water vapor condenses out on the fins and the water droplets are trapped by the fins 68. If necessary, a droplet eliminator may be incorporated to avoid passing through with the now stripped air stream at 72.

The liquid condensed by the condenser 64 and precipitated from the air stream in chamber 36 are collected with a suitable drain system 74 and passed to a suitable storage container 76. The condensed liquid contains most of the vapors emanated by bath 12 so that the air stream 72 can be either recirculated via a duct 77 into the space 14 of the plant 16 or exhausted to ambient via duct 78.

A sensor 84 is employed to detect the presence and amount of any vapors after passage through the condenser 64. In the event of a breakdown or an emergency condition a signal from sensor 84 and present on line 86 after signal processing at 87 can be used, as suggested by lines 88, 88' to operate actuator/controllers 89, 89' to control dampers 90, 92, respectively. The return damper 90 in such case would be closed and exhaust damper 92 could be opened to exhaust the air stream to ambient through duct 78.

Make-up air, when necessary, can be provided via a suitable damper 94. Coolant for condenser 64 is obtained from conventional refrigeration equipment 96. A control 100 is provided for foggers 40.1 and 40.2. The control may include such conventional components as pressure regulators, safety valves, flow meters, and the like necessary to operate foggers 40 in the desired operating conditions. Typically, operating conditions may include an air pressure of about 80 psi and a water pressure of about 60 psi. Water and air are supplied at desired higher pressures in lines 102, 104 respectively from suitable sources such as a pump and air compressor, not shown.

A particular advantage of a system 10 in accordance with the invention is the use of an enhanced mixing activity within the fogging chamber 36 while using a significantly lesser amount of liquid such as water For example, where a conventional air washer may use from about 0.75 to about 5. gallons of water per minute per square foot, the use of foggers which are capable of inducing a large amount of mixing action can reduce the water requirement to a level of the order of 3 gallons per hour per square foot. This reduction significantly reduces the processing and costs of handling the waste water. Such enhanced mixing is particularly achieved by using foggers capable of inducing a substantial amount of secondary air flow.

Another advantage of system 10 is the use of an air preheater 105 placed ahead of chamber 36 to heat the air stream 34. The heater 105 can be regulated by a controller 106 to deliver a particular amount of heat depending upon the temperature of the air stream 34 as sensed by temperature sensor 107. Alternately, the latent heat of vaporization of the air steam 34 can be controlled to a particular level by sensing the air stream temperature downstream of heater 105 and prior to chamber 36 as shown in FIG. 5 and controlling to a particular temperature level.

When the air temperature is increased by heater 105, the quantity of scrubbing water that can be vaporized is increased. For example, if the air stream 34 is at a temperture of 70° F. and this is increased to 100° F., then by following the curves of a standard psychrometric chart, the amount of moisture that can be vaporized in chamber 36 is increased by almost 50%. The additional moisture content is then available for removal of containment vapors which are scrubbed out of the air stream with the condenser 64.

Figure 5:
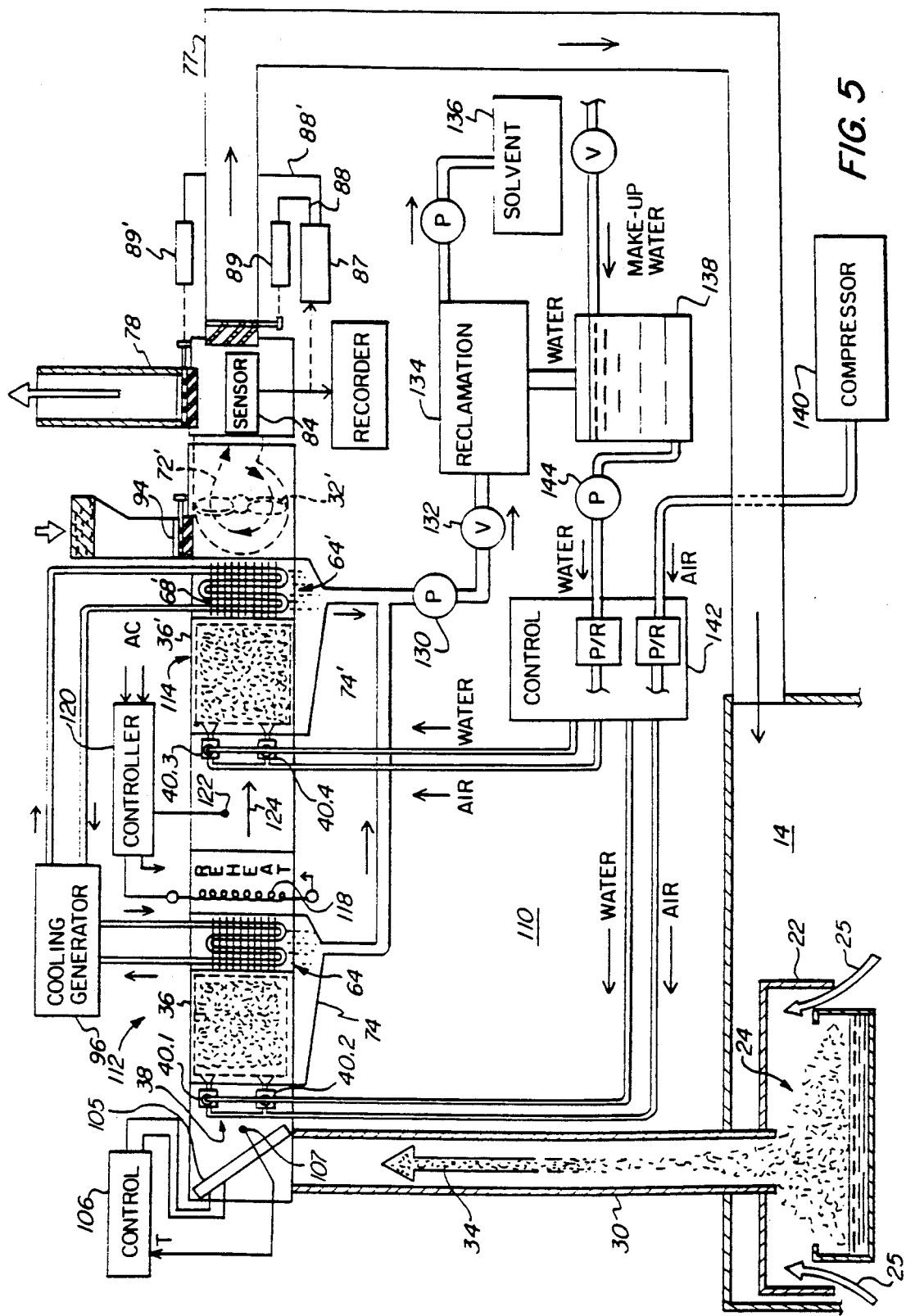
FIG. 5 is a schematic representation and crossectional view of another system in accordance with the invention for removing solvent vapors from an airstream in accordance with the invention.

FIG. 5 illustrates a solvent remover system 110 with which an even larger percentage of solvent vapors such as 24 can be removed. System 110 is similar to stripper system 10 of FIG. 1. Hence, similar numerals identify like components as described with reference to FIG. 1.

In system 110, a pair of solvent strippers 112, 114 like 10 are placed in tandem so that the stripped air stream flow from stripper system 112 becomes the input air flow for stripper system 114. Since the air temperature at the output of the cooling condenser 64 is too low for proper operation of stripper system 114, a reheater 118 is used to reheat the air. The temperature to which the air is raised can be regulated by a controller 120 which responds to the flow temperature as sensed by a temperature sensor 122.

The temperature to which the air is reheated is selected commensurate with an effective operation of the successive stripper system 114. Generally, the temperature is the same as that of the air flow 34 in duct 30. Typically, this is about 70° F., though variations from that can be used as this appears desirable.

The reheated air flow contains residual vapors that were not removed by system 112. As the reheated air flow, as represented by arrow 124, enters stripper system 114, it enters fog chamber 36' which is humidified by foggers 40.3 and 40.4, and others in a manner similar as is done in the stripper systems 10 and 112. Hence, again a supersaturated condition is created in chamber 36' causing molecules of vapor 24 to adhere to or become otherwise associated with water molecules, either inside chamber 36' or on the wetted surfaces of fins 68' of the cooling condenser 64'.

The effect of the second condenser 64' is similar to the one in system 110, causing a removal of most of the humidification and the remaining vapors present at the output of stripper system 112. With the sequential systems 112, 114, a high degree of effectiveness can be achieved.

For example, preliminary tests on a single pass vapor removal set-up similar to that system shown in FIG. 1, the following results were obtained as listed in Table 1 using water as the liquid introduced by the foggers.

TABLE I

| Test | Mat'l | A Velocity M/S | B Air Volume Normalized Nm³/hr | C Input Quantity of Solvents kg/hr | Concentration PPM mg/Nm³ D Input | E Output | Removal Efficiency % Removed D − E D |
|---|---|---|---|---|---|---|---|
| 1 | M | 9.2 | 2340 | 15.9 | 6800 | 4790 | 29.50% |
| 2 | M | 9.4 | 2391 | 1.1 | 466 | 50 | 89% |
| 3 | M | 9.2 | 2340 | 2.12 | 902 | 500 | 45% |
| 4 | A | 9.2 | 2340 | 0.046 | 19 | 1 | 94.91% |
| 5 | IP | 9.2 | 2340 | 0.028 | 12 | 3 | 74.93% |
| 6 | M | 9.1 | 2314 | 6.6 | 2880 | 1120 | 61% |
| 7 | A | 9.1 | 2314 | 0.011 | 4.8 | Not Detect. | 100.00% |
| 8 | IP | 9.1 | 2314 | 0.02 | 8.4 | Not Detect. | 100.00% |
| 9 | M | 9.2 | 2340 | 12.6 | 5500 | 4000 | 27% |
| 10 | M | 9.1 | 2314 | 4.4 | 1930 | 854 | 55.09% |

M = Methylene Chloride, $CH_2CL_2$
A = Acetone
IP = Isopropylalcohol

For example, if system 112 removes as per test 3 in Table I, 45% of the methylene chloride vapors, then the input to the second system 114 would be the concentration of 500 PPM from the first system. The second system 114, working with a lower input concentration, would be more effective in the removal according to the second test leaving a remaining concentration of somewhat more than about 50 PPM. The combined effect of both systems approaches 90% or better or, in effect, a removal ratio of about 18 to 1. The advantage of using several systems in tandem is that greater flexibility and effectiveness of the combined systems is achieved at relatively reasonable costs. The first system 112 could be made to scrub solvent with a different liquid than water and the second system 114 used to remove most of this different liquid.

In the system 110 as shown in FIG. 5, water is the stripping or scrubbing agent. The condensed water from the condensers 64, 64' is pumped by pump 130 through a valve 132 to a separation system 134. This may be a closed solvent remover in which solvent is reclaimed in a storage tank 136 and the cleaned scrubbing water is made available for reuse in system 110 by collecting it in a tank 138. Make up water is supplied to tank 138. Solvent separation system 134 can be of a conventional design, depending upon the type of solvent.

Operation of foggers 40.1–40.4 employs devices such as a compressor 140 and a conventional control panel 142 with a suitable pressurized supply of water obtained with pump 144.

Having thus described the invention in several embodiments, its advantages can be appreciated. Variations of the embodiments can be made without departing from the scope of the invention as determined by the following claims.

What is claimed is:

1. A method for removing solvent vapors from air in an enclosure where the solvent is miscible with or soluble in or has an affinity for a scrubbing liquid comprising the steps of:
   generating a flow of air containing the vapors;
   passing the flow of air through a fogging chamber;

injecting a scrubbing liquid in the form of fog droplets into the fogging chamber and with an amount and distribution of the fog so as to produce a supersaturated condition formed of scrubbing vapor and droplets within and throughout the air flow of the fogging chamber so as to cause contact between vapor molecules and scrubbing droplets;

passing scrubbing liquid saturated air flow from the fogging chamber past a cooling condenser;

cooling the condenser to a sufficiently low temperature so as to cool the saturated air flow to a temperature at which a substantial amount of the scrubbing liquid in the air flow is condensed out to wet the condenser and enable solvent vapors in the air flow to contact wettened surfaces of the condenser; and collecting scrubbing liquid condensed out by the condenser with captured solvent to complete removal of the vapors from the air flow.

2. The method for removing vapors as claimed in claim 1 wherein the step of injecting the scrubbing liquid is accompanied with a sufficient amount of turbulence and mixing of air and scrubbing fog in the fogging chamber so as to cause a substantial amount of the vapor in the air flow in the fogging chamber to establish contact with scrubbing vapor droplets which are then condensed out on the condenser surfaces.

3. The method for remvoing vapors as claimed in claim 2 and further comprising:

applying pressurized air and scrubbing liquid to a plurality of ultrasonic foggers located inside the fogging chamber to produce said fog, with said air being pressurized at a level in the range from about 60 psi to about 100 psi and the pressure applied to said water is commensurately below the air pressure.

4. The method for removing vapors as claimed in claim 1 wherein the removal of vapor from the air flow is sufficient to enable the air flow from which the vapors have been scrubbed to be returned to the enclosure and returning said scrubbed air flow to said enclosure. and further comprising:

5. The method as claimed in claim 1 and further comprising the steps of:

applying heat to the scrubbed air flow to reheat it to a desired temperature;

passing the reheated air flow into a second fogging chamber;

injecting a scrubbing liquid in the form of fog droplets into the second fogging chamber to produce a sufficient supersaturation level to cause contact between vapor molecules and scrubbing droplets;

passing scrubbing liquid saturated air flow from the second fogging chamber past a second cooling condenser;

cooling the second cooling condenser to a sufficiently low temperature so as to cause scrubbing liquid to condense out of the air flow from the second saturation chamber to wet the condenser and enable vapors in the air flow to contact condensed scrubbing liquid; and collecting condensed scrubbing liquid and associated vapor molecules so as to enhance the removal of vapors from the air flow.

6. The method for removing vapors from air as claimed in claim 1 and further comprising the steps of:

removing solvent collected with the condensed scrubbing liquid and storing the solvent; and applying said condensed scrubbing liquid from which the solvent is removed to saturate the fogging chamber.

7. The method for removing solvent vapors as claimed in claim 1 and further comprising the steps of:

sensing solvent vapors remaining in the stripped air flow emanating from the fogging chamber and producing a vapor level signal indicative thereof; and recording said vapor level signal.

8. The method for removing solvent vapors as claimed in claim 7 and further comprising the step of:

discharging the air flow from the saturation chamber to ambient when the sensed solvent vapor level exceeds a maximum permissible level.

9. A system for removing vapors of a solvent from an air stream drawn from a local region in a work place, comprising:

means for producing a fogging chamber having an entrance and a discharge end;

means for drawing a stream of air containing solvent vapors from a region around a source of such vapors and through the fogging chamber from its entrance to the discharge end;

means for producing a scrubbing vapor throughout the fogging chamber in an amount sufficient to create a supersaturated condition of scrubbing liquid droplets and vapor and with the scrubbing droplets and vapor being sufficiently distributed throughout the fogging chamber and with sufficient mixing turbulence and induced recirculation so as to substantially reduce the ability of solvent vapors to bypass contact with the scrubbing liquid;

means for cooling the air stream laden with scrubbing vapor and droplets to a temperature sufficient to remove moisture from the air stream by condensing the scrubbing vapors and droplets and capture the scrubbing liquid droplets on wetted surfaces so as to produce an air stream from which a substantial amount of the solvent vapors has been removed; and means for collecting the condensed scrubbing liquid with the solvent that was removed from the air stream.

10. The system for removing vapors of a solvent from an air stream as claimed in claim 9 wherein the cooling means removes a sufficient amount of the solvent vapors from the air stream for its reuse; and means for returning the air stream emanating from the cooling means to the work place.

11. The system for removing vapors of a solvent from an air stream as claimed in claim 10 and further including:

means for sensing the presence of solvent vapors in the air stream after solvent vapor removal and produce a signal indicative thereof, and means for discharging the air stream to ambient when the sensed level of vapors exceeds a maximum tolerable level.

12. The system for removing vapors of a solvent from an air stream as claimed in claim 9 wherein said scrubbing vapor producing means includes a pluralitu of ultrasonic foggers of the type which produce a significant amount of air circulation for enhanced turbulence and mixing within the saturation chamber.

13. The system for removing vapors of a solvent from an air stream as claimed in claim 9 and further including:

means for reheating the air stream after it emerges from the cooling means to a temperature sufficient for another scrubbing operation;

means for producing a second fogging chamber;

means for producing scrubbing droplets throughout the second fogging chamber in an amount sufficient to create a saturated condition of scrubbing liquid droplets and vapor and with the scrubbing droplets and vapor being sufficiently distributed throughout the second fogging chamber and with sufficient turbulence and mixing so as to substantially reduce the ability of solvent vapors to bypass contact with scrubbing liquid; and second means for cooling the air stream laden with scrubbing vapor and emerging from the second fogging chamber to a temperature sufficient to remove moisture from the air stream by condensing the scrubbing vapors and capture scrubbing droplets on wetted surfaces so as to produce an air stream from which an enhanced amount of solvent vapors has been removed.

14. The system for removing vapors of a solvent from an air stream as claimed in calim 13 and further including:

means for recirculating the air stream from the second cooling means to the work place.

15. The system for removing vapors of a solvent from an air stream as claimed in claim 9 further including:

means for separating solvent condensed out by the cooling means from condensed scrubbing liquid; and means for supplying the condensed scrubbing liquid to the cooling means.

16. The system for removing vapors of a solvent from an air stream as claimed in claim 9 wherein the cooling means includes a cooling coil with fins and having a sufficient number of turns to substantially condense out the scrubbing droplets and vapor from the air stream; and means for establishing a counterflow of a cooling medium through said cooling coil.

* * * * *